US007550426B2

(12) United States Patent
Wagner et al.

(10) Patent No.: US 7,550,426 B2
(45) **Date of Patent: *Jun. 23, 2009**

(54) ACETYLATED THERAPEUTIC PROCYTOTOXINS

(75) Inventors: Thomas E. Wagner, Greer, SC (US); Xianzhong Yu, Mauldin, SC (US)

(73) Assignee: GHC Research Development Corporation, Greenville, SC (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/131,443

(22) Filed: May 18, 2005

(65) Prior Publication Data

US 2006/0264364 A1 Nov. 23, 2006

(51) Int. Cl.

| | |
|---|---|
| ***A61K 38/16*** | (2006.01) |
| ***A61K 38/33*** | (2006.01) |
| ***A61K 45/00*** | (2006.01) |
| *C07K 14/195* | (2006.01) |
| *C07K 14/435* | (2006.01) |

(52) U.S. Cl. ............................ 514/2; 514/12; 530/300; 530/324; 530/402; 530/820; 530/822; 530/823; 530/825

(58) Field of Classification Search ....................... None
See application file for complete search history.

(56) References Cited

U.S. PATENT DOCUMENTS 7,232,800 B2 * 6/2007 Sun et al. ....................... 514/12

FOREIGN PATENT DOCUMENTS

WO WO 01/85777 * 11/2001

OTHER PUBLICATIONS

Warren et al (Cancer Research, 2001, vol. 61, pp. 6783-6787).*
Doi et al (Arhives of Biochemistry and Biophysics, 2001, vol. 395, pp. 85-93).*
Blondelle et al., (1991) *Biochemistry* 30: 4671-4678.
Dempsey et al., (1991) *FEBS Lett.* 281: 240-244.
Argiolas, A., and Pisano, J., 1985, *J. Biol. Chem.* 260, 1437-1444.
Young et al., (1982) *J. Exp. Med.* 156: 1677.
Lynch et al., (1982) EMBO J 7: 801.
Young & Cohn, (1985) *J. Cell Biol.* 29: 299.
Rosenberg et al., (1989) *Molec. Biochem. Parasit.* 33: 237.
Jansson et al., (1994) *Science* 263: 1440.
Leippe et al., (1994) *Proc. Natl. Acad. Sci. USA* 91: 2602.
Andra et al., *FEBS Letters*, 385 (1996), pp. 96-100.
Shai et al., (1996) *J. Biol. Chem.* 271-7305-7308.
Werkmeister et al. (1993), *Biochim. Biophys. Acta* 1157: 50-54.
Horosczewicz et al. (1983), *Cancer Res.* 43: 1809-1818.
Pinto et al. (1999), *The Prostate J.* 1: 15-26.
Wright et al. (1995), *Urol. Oncol.* 1: 18-28.
Lopes et al., (1990), *Cancer Res.* 50: 623-6428.
Troyer et al., *Int. J. Cancer* 62: 552-558.
Andreu et al., (1983) *Proc. Natl. Acad. Sci USA* 80: 6475-6479.
Andreu et al., (1985) *Biochemistry* 24: 1683-1688.
Fink et al. (Jun. 1989) *Int. J. Peptide Protein Res.* 33: 412-421.
Fink et al., (1989) *J. Biol. Chem.* 264: 6260-6267.
Wallace, B M, Lasker, J S, *Science*, 260:912-912 (1992).

* cited by examiner

*Primary Examiner*—Karen A Canella
(74) *Attorney, Agent, or Firm*—Foley & Lardner LLP

(57) ABSTRACT

A class of procytotoxic agents is characterized by a capability to kill with target cell-specificity. Such an aspect can be a pore-forming protein which has at least one lysine residue, modified by a peptide linkage to an amino acid residue, via the epsilon amino group, and an acetyl group. These agents are useful in treating cancer, especially prostate cancer.

22 Claims, 2 Drawing Sheets

SEQUENCE LISTING

```
<160> NUMBER OF SEQ ID NOS: 11

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 1

Gly Phe Ile Ala Thr Leu Cys Thr Lys Val Leu Asp Phe Gly Ile Asp
  1               5                  10                  15

Lys Leu Ile Gln Leu Ile Glu Asp Lys
             20                  25


<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 2

Gly Ile Gly Ala Val Leu Lys Val Leu Thr Thr Gly Leu Pro Ala Leu
  1               5                  10                  15

Ile Ser Trp Ile Lys Arg Lys Arg Gln Gln
             20                  25


<210> SEQ ID NO 3
<211> LENGTH: 25
<212> TYPE: PRT
<213> ORGANISM: Entamoeba histolytica

<400> SEQUENCE: 3

Gly Phe Ile Ala Thr Leu Cys Thr Lys Val Leu Asp Phe Gly Ile Asp
  1               5                  10                  15

Lys Leu Ile Gln Leu Ile Glu Asp Lys
             20                  25


<210> SEQ ID NO 4
<211> LENGTH: 37
<212> TYPE: PRT
<213> ORGANISM: Antheria pernyi

<400> SEQUENCE: 4

Lys Trp Lys Leu Phe Lys Lys Ile Glu Lys Val Gly Gln Asn Ile Arg
  1               5                  10                  15

Asp Gly Ile Ile Lys Ala Gly Pro Ala Val Ala Val Leu Gly Gln Ala
             20                  25                  30

Thr Gln Ile Ala Lys
         35
```

-continued

<210> SEQ ID NO 5
<211> LENGTH: 35
<212> TYPE: PRT
<213> ORGANISM: Antheria pernyi

<400> SEQUENCE: 5

Lys Trp Lys Ile Phe Lys Lys Ile Glu Lys Val Gly Arg Asn Ile Arg
1 5 10 15

Asn Gly Ile Ile Lys Ala Gly Pro Ala Val Ala Val Leu Gly Glu Ala
20 25 30

Lys Ala Leu
35

<210> SEQ ID NO 6
<211> LENGTH: 36
<212> TYPE: PRT
<213> ORGANISM: Antheria pernyi

<400> SEQUENCE: 6

Trp Asn Pro Phe Lys Glu Leu Glu Lys Val Gly Gln Arg Val Arg Asp
1 5 10 15

Ala Val Ile Ser Ala Gly Pro Ala Val Ala Thr Val Ala Gln Ala Thr
20 25 30

Ala Leu Ala Lys
35

<210> SEQ ID NO 7
<211> LENGTH: 26
<212> TYPE: PRT
<213> ORGANISM: Apis mellifera

<400> SEQUENCE: 7

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments

<400> SEQUENCE: 8

Gly Phe Ile Ala Thr Leu Cys Thr Lys Val Leu Asp Phe Gly Ile Asp
1 5 10 15

Lys Leu Ile Gln Leu Ile Glu Asp Lys
20 25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments -continued

<400> SEQUENCE: 9

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments

<400> SEQUENCE: 10

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(4)
<223> OTHER INFORMATION: May or may not be present

<400> SEQUENCE: 11

Glu Glu Glu Glu
1

ACETYLATED THERAPEUTIC PROCYTOTOXINS

BACKGROUND

1. Field of the Invention

This invention relates to methods and compositions for treating cancer. Specifically, the invention relates to the use of a procytotoxin that can be converted to an acetylated cytotoxin in a tumor-cell specific manner, such that the tumor cell is destroyed by the activated cytotoxin.

2. Background of the Invention

Present methods for tumor treatment, especially for cancer treatment, remain sub-optimal and often are accompanied by severe complications. In fact, virtually all of the known therapies have serious adverse side effects, most often caused by the lack of specificity and thoroughness in the destruction or removal of tumor or cancer cells.

For example, surgery, a common procedure for removing cancerous cells from a patient, is often incomplete, and it disfigures the patient or interferes with normal bodily functions. Similarly, chemotherapy and radiation treatment can indiscriminately destroy normal cells, causing unwanted side-effects while leaving many cancer cells unaffected. Chemotherapeutic agents, especially antimetabolites, while effective to varying degrees against cancer cells that are continuously undergoing or preparing for mitosis, are not effective against cancer cells that are in the resting ($G_0$) stage.

Cancer treatment is most effective when cancer cells can be eliminated as completely as possible from the patient's body. Thus, continuous or consecutive dosages are often administered to the patient. Because most available chemotherapeutic agents are also toxic to normal cells, the dose of cytotoxic drug is adjusted to the limits of tolerance to achieve the maximum destruction of malignant cells, and the interval between doses must be such that the rate of tumor re-growth does not exceed tumor killing. Accordingly, in order to achieve increased efficiency, the chemotherapeutic agents should have high target-cell specificity and high target-cell toxicity or potency.

To this end, the inventors of the present invention previously discovered compositions and methods for treating cancer in a site-specific manner. In particular, U.S. patent application Ser. No. 09/851,422 describes a modified cytotoxic peptide that can be rendered non-toxic by the addition, via a peptide bond, of at least one amino acid residue to the ε-amino group of a lysine residue in the cytotoxic peptide. In the presence of a specific target cell enzyme, the peptide bond is cleaved and the cytotoxic peptide resumes its toxic properties.

But since certain effective cancer treatment methods are, in part, dependent on tumor type and location, and certain treatment methods are more suited for a specific route of administration, there is always a need for additional treatment agents and methods that can be used so as to expand the possible options available for successfully combating cancer. The present invention fulfills these needs and further provides other related advantages.

SUMMARY OF THE INVENTION

Therefore, it is an object of the present invention to provide compositions and methods for treating cancer, especially via parenteral, and more particularly, intraperitoneal, subcutaneous and intravenous injection. To this end, an acetylated procytotoxin is provided which is typically made up of a modified cytotoxic peptide bound through its ε-amino group to one or more amino acid residues. In different embodiments, one, two, or more additional amino acid residues are bound to the amino acid attached to the lysine, and the free amino group of the additional amino acid residue(s) is acetylated. Generally preferred cytotoxins include Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, E1 Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perforin, perfringolysin O, theta-toxin, of *Clostridium perfringens*, phallolysin, phallotoxin, streptolysin, and analogs and derivative thereof.

Particularly preferred procytotoxins have the following structures: (1) Gly-Phe-Ile-Ala-Thr-Leu-Cys-Thr-Lys{R}-Val-Leu-Asp-Phe-Gly-Ile-Asp-Lys{R}-Leu-Ile -Gln-Leu-Ile-Glu-Asp-Lys{R} (SEQ ID NO: 1), and (2) Gly-Ile-Gly-Ala-Val-Leu-Lys(R)-Val-Leu-Thr-Thr-Gly-Leu-Pro-Ala-Leu-Ile-Ser-Trp-Ile-Lys{R}-Arg-Lys{R}-Arg-Gln-Gln, (SEQ ID NO: 2), wherein {R} is independently selected from the group consisting of [ε-γ]-Glu-Ac and [ε-γ]-Glu -[α-γ]-$(Glu)_{1-3}$-Ac (SEQ ID NO: 11), wherein [ε-γ] represents a peptide bond between the epsilon amino group of lysine and the gamma carboxyl group of the adjacent glutamate and [α-γ] represents a peptide bond between the alpha amino group of the first glutamate and the gamma carboxyl group of the second glutamate, and Ac represents an acetylated free amino group of the adjacent glutamate. Thus, in one embodiment, procytotoxin comprises the following structure: (1) Gly-Phe-Ile-Ala-Thr-Leu-Cys-Thr-Lys-Val-Leu-Asp-Phe-Gly-Ile-Asp-Lys-Leu-Ile-Gln-Leu-Ile -Glu-Asp-Lys-{[ε-γ]-Glu-[α-γ]-(Glu)-Ac}-$CONH_2$ (SEQ ID NO: 8). Modifications at each R position need not occur, but a modification at at least one R position must occur. In one embodiment, at least the C-terminal lysine is modified.

Also provided, in achieving this objective of the invention, are pharmaceutical compositions that, in general, contain an inventive procytotoxin and a pharmaceutically acceptable excipient.

Further, methodology is provided for destroying a target cell selectively. This approach typically entails bringing an inventive procytotoxin into contact with a target cell, which generally will have a cell-surface glutamate peptidase, such as prostate specific membrane antigen. Thus, on one embodiment, a prostate cancer cell is the target cell.

Further to the same embodiment, a method for treating prostate cancer is provided. In general, the method comprises administering to a patient in need, a pharmaceutical composition containing a procytotoxin according to the invention. In one embodiment, the compositions described herein are parenterally administered and in particular, intraperitoneally administered. Preferred compositions contain procytotoxins based on amoebapore, a melittin or a cytolytic peptide derived therefrom.

DETAILED DESCRIPTION OF THE INVENTION

Figure 1:
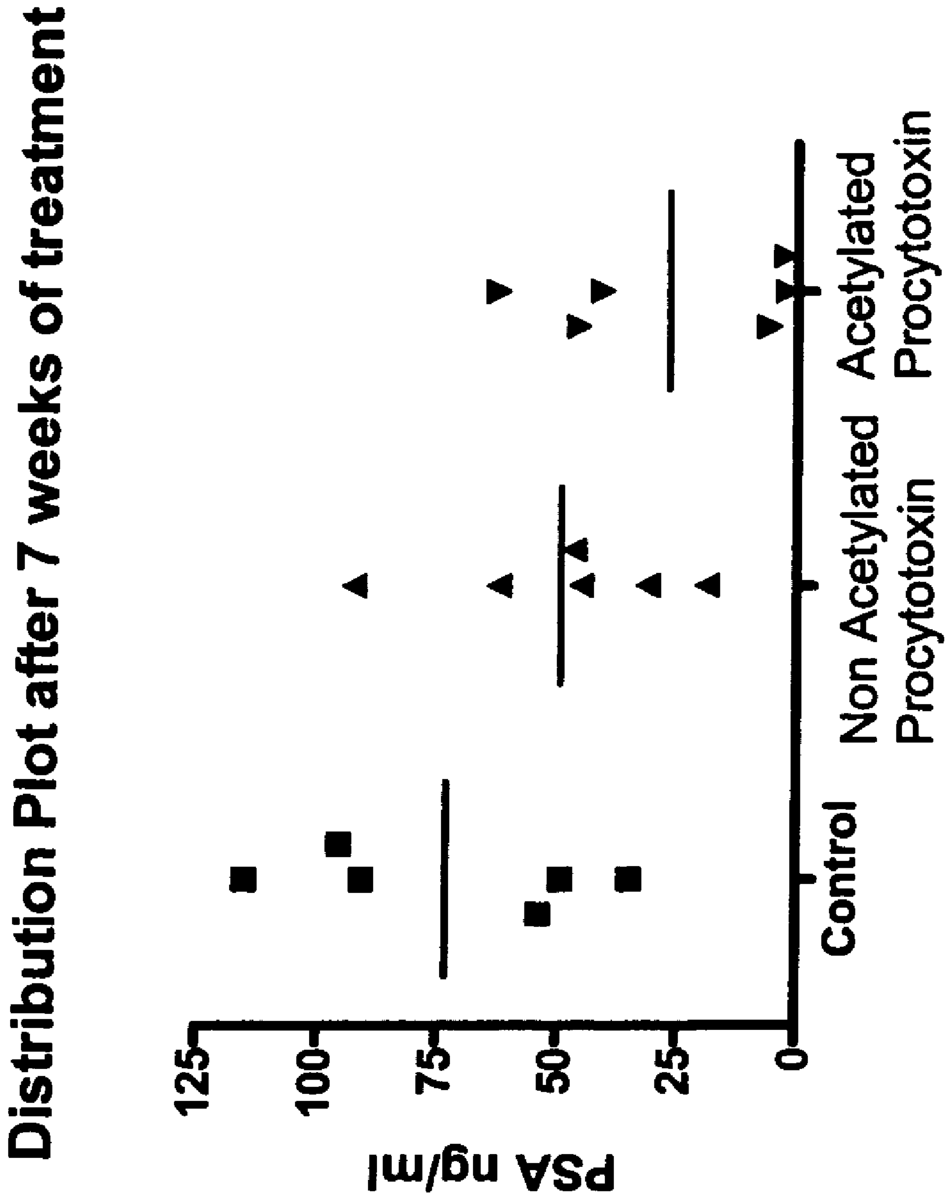
FIG. 1. Graph of plasma PSA levels following 7 weeks of intraperitoneal injection of a non-acetylated procytotoxin or an acetylated procytoxin into a mouse model for prostate cancer.
Figure 2:
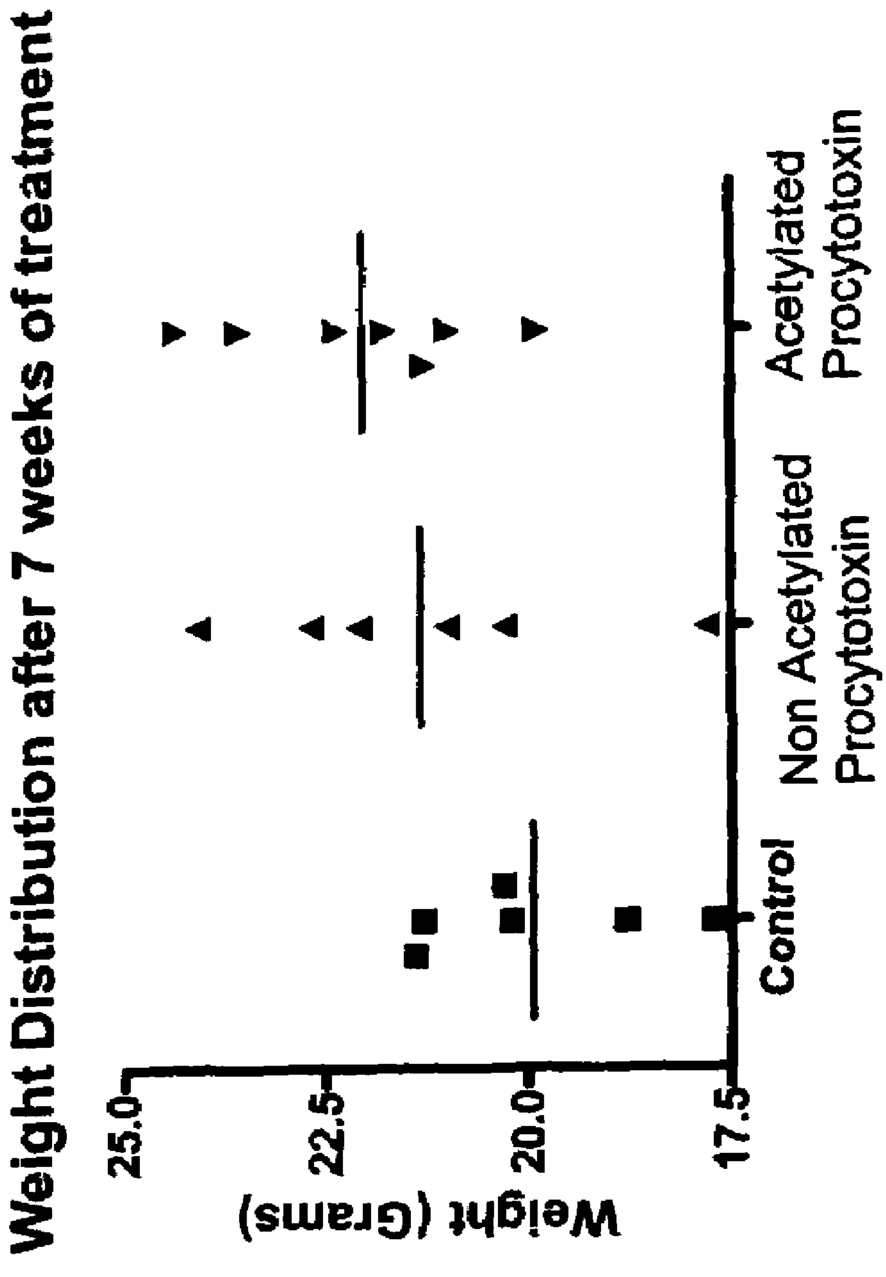
FIG. 2. Graph of mouse weight following 7 weeks of intraperitoneal injection of a non-acetylated procytotoxin or an acetylated procytoxin into a mouse model for prostate cancer.

Unless otherwise stated, "a," "an," and "the" mean one or more.

The present invention provides a pharmaceutical composition and a method for selectively destroying a target cell, like a cancer cell. The pharmaceutical composition comprises a procytotoxin that can be activated in a target cell-specific manner, thereby killing, destroying or eliminating the target cell.

A procytotoxin according to the present invention is a compound that is not itself cytotoxic but may be converted into a cytotoxin. A cytotoxin is a substance that is harmful, destructive or deadly to a cell. A preferred cytotoxin according to the present invention kills or otherwise eliminates the target cell from a patient with high potency.

The pharmaceutical composition according to the instant invention generally does not affect nontarget cells. In a preferred embodiment, target cell-specific activation of the procytotoxin occurs only at or near the target cells. When the pharmaceutical composition is used for treating cancer cells, the procytotoxin remains in an inactive state, thus is nontoxic, until it reaches the cancer site. In fact, the compositions of the present invention do not act intracellularly to cause cell toxicity. Thus, in the case of cancer treatment, the procytotoxin is activated at the surface of the cancer cells, thereby achieving high specificity in the destruction of target cells versus normal cells. Once the procytotoxin is activated in a target cell-specific manner, the high potency of the cytotoxin ensures that the pharmaceutical composition achieves a thorough destruction of the target cells.

Cytotoxic Peptides

According to one embodiment of the invention, a procytotoxin comprises a cytotoxic peptide that has been modified to render it non-toxic, as detailed below. Many naturally occurring and synthetic cytotoxic peptides are known in the art. Some are useful as therapeutic agents against pathogenic bacteria and other classes of microorganisms; they may be isolated from insects, frogs and other animals. Specific examples include alamethicins, attacins, bactenecins, cecropins (see Table 1 the amino acid sequences of cecropins A, B and C), CytA and CytB of *Bacillus thurigiensis*, defensins, enterocin L50 (pediocin L50), lantibiotics, magainins, PGLa, protegrins, sapecin, and sarcotoxin.

A preferred cytotoxic peptide is a cytolytic peptide. Cytolytic peptides, also known as channel-forming peptides, typically disrupt cell membranes, causing cell lysis and death upon contact. Many naturally occurring cytolytic peptides from microorganisms, insects and higher animals are generally known. They often are called hemolysins because they lyse red blood cells as well as other eukaryotic cells. These toxins include Ae I and other cytolysins of sea anemone, aerolysin, amatoxins, amoebapores, amoebapore homologs from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxins, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin and neokyotorphin fragments (1-4), NK-lysin, paradaxins, perforin (especially its amino terminus), perfringolysin O (PFO or theta-toxin) of *Clostridium perfringens*, phallolysins and phallotoxins, and streptolysins. Some hemolysins like melittin are also known to kill bacteria.

Many cytolytic peptides are pore-forming toxins, belonging to a group of cytotoxins that associate with cell membranes, nonspecifically or to specific receptors, and form transmembrane pores of discrete size. Most toxic pore-forming peptides employ common features for their cell lysis activity. For example, a great number of these toxins lyse cells through a "barrel-stave" mechanism, in which monomers of the toxin bind to and insert into the target membrane and then aggregate like barrel staves surrounding a central, water filled pore. This pore causes rapid and irreversible electrolyte imbalance of the target cell leading to its destruction.

Most pore-forming peptides that act on both mammalian and bacterial cells require an amphipathic alpha-helical structure and a net positive charge for their cytolytic activity. A strong electrostatic interaction between the cationic portion of the peptide and the lipid headgroups weakens the membrane, facilitating insertion of the hydrophobic alpha-helical peptides. Accordingly, a particularly preferred cytotoxic peptide according to the invention is a cytolytic, linear α-helical peptide. Generally these cytotoxic peptides, in their native form, will have a net positive charge, which contributes to their cytolytic activity.

According to one embodiment of the invention, the cytolytic peptide is melittin or an analog or derivative thereof. Melittin is isolated from bee venom and is a 26 amino acid amphiphilic alpha-helix (Blondelle et al., (1991) *Biochemistry* 30: 4671-4678; Dempsey et al., (1991) *FEBS Lett.* 281: 240-244). The amino acid sequence of melittin is shown in Table 1. Residues 1-20 are predominantly hydrophobic and residues 21 to 26 are hydrophilic and basic. Melittin has antibiotic activity, but in mammals it is lytic for leukocytes, red blood cells and a wide variety of other cells. Compounds similar to melittin, which are also within the scope of the invention, include bombolitin from bumblebee venom (17 amino acid amphiphilic alpha-helix), mastoparan from wasp venom (14 amino acid amphiphilic alpha-helix) and crabrolin from hornet venom (13 amino acid amphiphilic alpha-helix) Argiolas A. and Pisano J.J., 1985, J. Biol. Chem. 260, 1437-1444).

TABLE 1

| Amino Acid Sequence of Selected Cytolytic Peptides |
|---|
| Amoebapore Helix 3 (*Entamoeba histolytica*) |
| $NH_2$-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-$CONH_2$ (SEQ ID NO:3) |
| Cecropin A (*Antheria pernyi*) |
| $NH_2$-Lys-Trp-Lys-Leu-Phe-Lys-Lys-Ile-Glu-Lys-Val-Gly-Gln-Asn-Ile-Arg-Asp-Gly-Ile-Ile-Lys-Ala-Gly-Pro-Ala-Val-Ala-Val-Val-Gly-Gln-Ala-Thr-Gln-Ile-Ala-Lys-COOH (SEQ ID NO:4) |
| Cecropin B (*Antheria pernyi*) |
| $NH_2$-Lys-Trp-Lys-Ile-Phe-Lys-Lys-Ile-Glu-Lys-Val-Gly-Arg-Asn-Ile-Arg-Asn-Gly-Ile-Ile-Lys-Ala-Gly-Pro-Ala-Val-Ala-Val-Leu-Gly-Glu-Ala-Lys-Ala-Leu-COOH (SEQ ID NO:5) |

TABLE 1-continued

| Amino Acid Sequence of Selected Cytolytic Peptides |
|---|
| Cecropin D (*Antheria pernyi*) |
| $NH_2$-Trp-Asn-Pro-Phe-Lys-Glu-Leu-Glu-Lys-Val-Gly-Gln-Arg-Val-Arg-Asp-Ala-Val-Ile-Ser-Ala-Gly-Pro-Ala-Val-Ala-Thr-Val-Ala-Gln-Ala-Thr-Ala-Leu-Ala-Lys-COOH (SEQ ID NO:6) |
| Melittin (*Apis mellifera*) |
| $NH_2$-Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-COOH (SEQ ID NO:7) |

Another preferred pore-forming peptide, according to the instant invention, is amoebapore, a 77-residue pore-forming peptide from the amoebae *Entamoeba histolytica* (Young et al., (1982) *J. Exp. Med.* 156: 1677; Lynch et al., (1982) EMBO J 7: 801; Young & Cohn, (1985) *J. Cell Biol.* 29: 299; Rosenberg et al., (1989) *Molec. Biochem. Parasit.* 33: 237; Jansson et al., (1994) *Science* 263: 1440). It has four alpha helices, from amino acids approximately 1-21, 25-36, 40-63 and 67-77, conventionally called helices 1, 2, 3, and 4, respectively.

Three isoforms of amoebapore are known: amoebapore A, B and C, respectively. This peptide is stabilized by three disulfide bonds and contains four mostly amphipathic alpha-helical structures. The third amphipathic helical structure (helix 3) retains the cytolytic activity similar to the wild type peptide. A synthetic peptide based on the sequence of its third amphipathic alpha helix have recently been shown to have cytolytic activity for nucleated cells at high concentrations (10-100 μM) (Leippe et al., (1994) *Proc. Natl. Acad. Sci. USA* 91: 2602). This peptide, depicted above in Table 1, represents a preferred cytolytic peptide.

Some representative pore-forming cytolytic peptides are selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, E1 Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perforin, perfringolysin O, theta-toxin, of *Clostridium perfringens*, phallolysin, phallotoxin, and streptolysin.

It is readily recognized that the above described cytolytic peptides may be modified or derivatized to produce analogs and derivatives which retain, or even exhibit enhanced, cytolytic activities. For example, Andra et al. disclose that shortened amoebapore analogs have enhanced antibacterial and cytolytic activities (*FEBS Letters,* 385 (1996), pp. 96-100, incorporated herein by reference in its entirety).

In designing such analogs or derivatives, the artisan will be informed by the foregoing discussion relating to the amphipathic alpha-helical structure and net positive charge that are implicated in the cytolytic activity. Thus, a skilled artisan is able to design amoebapore analogs, i.e., non-native forms never before known in nature, based on the observed homologies and known structure and properties of the native protein, to be used as a cytolytic peptide in accordance with the instant invention.

Modification and derivatization according to the instant invention include, but are not limited to, substitutions, additions or deletions that provide for functionally equivalent molecules. (Function may be assessed in accord with the working examples presented below.) Analogs and derivatives may also be made via modifications of side chains of amino acid residues of the cytotoxic peptides, preferably, with enhanced or increased functional activity relative to the native protein or polypeptide.

For example, analogs and derivatives of an amoebapore or other cytolytic peptides include, but are not limited to, those containing, as a primary amino acid sequence, all or part of the amino acid sequence the native peptide, such as with altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid. Because the terminal positive charges are thought to be involved in the cytolytic activity of the peptide, addition or substitution of a positively charged amino acid at the C-terminus is particularly contemplated to enhance its cytolytic potency.

Dimerization, truncation, diasteroisomers (D-amino acid-incorporated analogs) (Shai et al., (1996) *J. Biol. Chem.* 271-7305-7308), and combinations thereof may also be employed for producing derivatives and analogs of pore-forming peptides. For example, Werkmeister et al. (1993), *Biochim. Biophys. Acta* 1157: 50-54, discloses the effect of sequence and structural variations on the cytolytic activity of melittin, and is hereby incorporated by reference in its entirety.

Thus, in one embodiment, the modified cytotoxins may be dimerized, thereby creating a dimeric procytotoxin. The modification in at least one monomeric form of the dimeric procytotoxin comprises one lysine residue bound through its ε-amino group to one or more negatively charged amino acid residues. In another embodiment, the modification in at least one monomeric form of the dimeric procytotoxin comprises one lysine residue bound through its ε-amino group to one or more negatively charged amino acid residues, wherein the free amino group of the last negatively charged amino acid has been acetylated. In other words, if two glutamatic acid residues, for example, are added to the ε-amino group of a lysine residue in a cytotoxin, the free amino group of the second glutamic acid is acetylated. In another embodiment, the dimeric procytotoxin is a homodimer.

Methods for making dimers are known and a skilled artisan could readily make a dimer from the monomeric form of the procytotoxin by, for example, formation of an intermolecular disulfide bond between the sole cysteines on each monomer, or by other known methods.

The cytolytic peptides of the invention will normally contain from about 15 to about 40 amino acid residues. It is apparent to one skilled in the art that active low molecular weight peptides containing less than about 40 amino acids (or even less than about 30) are normally not difficult to synthesize chemically, while peptides with more than about 40 amino acids are relatively difficult to synthesize in pure form by chemical methods, and may be best prepared by fermentation or by recombinant DNA procedures from the appropriate genetic coding sequence.

A particular advantage of the useful peptides of this invention is that they are readily synthesized by solid phase methods and a variety of combinations are possible to achieve specifically required results. An advantage of using solid phase techniques is that the product can be directly synthesized with the C-terminus amidated or otherwise blocked, which is beneficial in forming the procytotoxins of the invention. For example, one procytotoxin requires formation of γ-glutamate peptide bonds which are readily produced by such chemical synthesis.

In another embodiment, the cytotoxin is amoebapore: $NH_2$-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-$CONH_2$(SEQ ID NO: 3).

Producing Procytotoxins

In order to enhance its therapeutic usefulness, a cytotoxin is modified according to the invention to render it to a non-toxic protoxin form. Numerous methods of modifications are available, the applicability of which will depend on the structural characteristics of the cytotoxin. A peptide, for example, may be added to either the N-terminus and/or the C-terminus of the cytotoxic peptide, such that the cytotoxic peptide is rendered non-toxic.

The inventors have surprisingly discovered that a procytotoxin comprising a modified cytotoxin that has at least one lysine residue bound via the epsilon amino group to another amino acid residue, wherein the other amino acid is acetylated, is more effective for use in treating a cancer via intraperitoneal injection than its non-acetylated procytoxin counterpart. Thus, a preferred method of modifying the cytotoxin of the present invention is to disrupt the alpha-helical structure of the cytotoxin, generally by sterically preventing the structure from forming and/or eliminating/neutralizing the positive charge of the pore-forming peptide. Because this charge is involved in its cytolytic activity, such neutralization renders the peptide non-toxic. It is envisioned that even a partial neutralization of this positive charge will be effective. In other words, a modified cytotoxin of the present invention preferably comprises the addition of a negatively charged acetylated amino acid to the ϵ-amino group of a lysine residue. The procytotoxin of the present invention is preferably used for treating a cancer via intraperitoneal, subcutaneous, or intravenous injection.

However, it also will be understood that steric determinants also may be important, in addition to or instead of, charge determinants. Thus, even if no neutralization is accomplished, some of the modifications below will result in steric alterations which will inactivate the toxin to create the protoxin.

More specifically, one means of preparing a procytotoxin is to modify one or more of lysine residues of the cytotoxin by, for example, the addition of a negatively charged amino acid residue via a peptide bond to the epsilon amino group of lysine, and acetylating the free amino group of the negatively charged amino acid. A preferred negatively charged amino acid is glutamate and more preferably, at least the C-terminal lysine contains the modification. In a particularly preferred embodiment the epsilon amino group of lysine is bound by a peptide linkage to the gamma carboxyl group of glutamate. The resultant free alpha carboxyl group in such a case is free to neutralize additional adjacent positively charged amino acids, like arginine, which is expected to further repress the activity of the cytotoxin. In some embodiments it is envisioned that more than one glutamic acid (poly-α-γ-glutamate) is added to a lysine. Thus, a peptide lysine is bound via an ϵ-γ linkage to a glutamate and that glutamate is bound to a second glutamate via an α-γ peptide bond. The free amino group on the second glutamate is preferably acetylated. Of course, the second glutamate may be bound to a third, and so on, but in that case, the free amino group of the last glutamate added is acetylated. Also, where a native molecule lacks a lysine, it may be added and modified, which still is expected to invoke the steric inhibition of toxin formation.

Generally, the amino acid added to the epsilon amino group using a peptide linkage will be the target of a membrane-associated protease. An increasing number of such enzymes are being identified which are correlated with neoplastic or preneoplastic states. Thus, they are convenient targets for therapy.

For example, particularly preferred embodiments of the present invention entail using a modified cytotoxin comprising one or more aceteylated γ-linked glutamate residues linked via a peptide bond to the epsilon amino group of at least one lysine, preferably the C-terminal-most lysine (hereinafter "acetylated γ-glutamate-masked amoebapore analog") to treat prostate cancer. It has been recently discovered that prostate cancer cells overexpress a type II transmembrane protein, the prostate specific membrane antigen ("PSMA"). PSMA has an intracellular epitope that is immunoreactive toward the 7E11C5 immunoglobulin G monoclonal antibody. Horosczewicz et al. (1983), *Cancer Res.* 43: 1809-1818. In prostate cancer patients, PSMA is highly expressed on malignant prostate epithelia, but only marginally on normal prostate glands, and to a lesser degree on benign prostatic hypertrophic epithelia. Pinto et al. (1999), *The Prostate J.* 1: 15-26; Wright et al. (1995), *Urol. Oncol.* 1: 18-28; Lopes et al., (1990), *Cancer Res.* 50: 623-6428; Troyer et al., *Int. J. Cancer* 62: 552-558.

The proteolytic domain of PSMA is located on the outside of the cell surface. Upon reaching the target cell, the procytotoxins of the invention, without having to be internalized by the target cell, will have their acetylated γ-linked glutamate residue(s) cleaved and removed, thereby permitting formation of the lytically active conformation. The procytotoxins thus are activated precisely at the desired site of action, the target cell. This direct effect on the target cell increases the effectiveness of the prostate cancer cell killing. The activated cytolytic peptide immediately inserts into the target cell, leaving it almost no chance of acting upon adjacent, non-target cells. (In fact, it is possible that one end of the peptide is already inserted into the membrane before it is activated by PSMA.) Furthermore, as discussed above, the activated toxin is neutralized by the membrane therefore after the lysis of the target cell, the cytolytic peptides remain adsorbed in the membrane debris of the target cell and do not leak and harm non-target cells.

Particularly preferred procytotoxins include a modified amoebapore, its analogs and its derivatives that contain one or more acetylated γ-glutamate-masked amoebapore analogs. A particularly preferred procytotoxin comprises a modified amoebapore that has the following structure: Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-{[ϵ-γ]-Glu-[α-γ]-(Glu-Ac} (SEQ ID NO: 8), wherein [ϵ-γ] represents a peptide bond between the epsilon amino group of lysine and the gamma carboxyl group of the adjacent glutamate and [α-γ] represents a peptide bond between the alpha amino group of the first glutamate and the gamma carboxyl group of the second glutamate, and Ac represents an acetyl group bound to the free amino group of the last glutamate.

Other particularly preferred procytotoxins include a modified melittin, its analogs and its derivatives that contain at least one acetylated γ-linked glutamate residue linked via a peptide bond to the epsilon amino group of a lysine (hereinafter "acetylated γ-glutamate-masked melittin analog"). As indicated in Table 1, melittin has two lysines and two adjacent arginines near its C-terminus. When one of the lysines is so masked, it is expected that the free alpha carboxyl group would act to neutralize the adjacent arginine, further contributing to the inhibition of the toxic activity of melittin. A particularly preferred procytotoxin comprises a modified melittin that has the following structure: Gly-Ile-Gly-Ala-Val-Leu-Lys-Val-Leu-Thr-Thr-Gly-Leu-Pro-Ala-Leu-Ile-Ser-Trp-Ile-Lys{[ϵ-γ]-Glu-Ac}-Arg-Lys-{[ϵ-γ]-Glu-Ac}-Arg-Gln-Gln (SEQ ID NO: 9), wherein -Lys-{[ϵ-γ]-Glu-Ac}-Arg- represents a peptide bond between the epsilon amino group of lysine and the gamma carboxyl group of the adjacent glutamate, wherein the free amino group of the adjacent glutamate is acetylated, and a standard peptide bond is formed between the lysine and arginine residues.

With regard to the terminology used herein, the artisan will recognize that a "standard" peptide bond is formed between the alpha carboxyl group of one amino acid with the alpha amino group of the next amino acid in the peptide chain and that peptide sequences are read from their amino-terminal end to their carboxyl-terminal end. For clarification, the following structures of glutamic acid and lysine are presented with the various groups named according to which carbon of the amino acid backbone they attach:

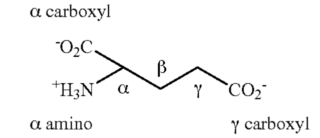

Glutamic Acid

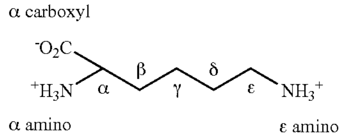

Lysine

In sum, a set of particularly preferred procytotoxins comprise a modified cytotoxin that can have the following structure: (1) Gly-Phe-Ile-Ala-Thr-Leu-Cys-Thr-Lys{R}-Val-Leu-Asp-Phe-Gly-Ile-Asp-Lys{R}-Leu-Ile-Gln-Leu-Ile-Glu-Asp-Lys{R} (SEQ ID NO: 1), or (2) Gly-Ile-Gly-Ala-Val-Leu-Lys{R}-Val-Leu-Thr-Thr-Gly-Leu-Pro-Ala-Leu-Ile-Ser-Trp-Ile-Lys{R}-Arg-Lys{R}-Arg-Gln-Gln (SEQ ID NO: 2), wherein {R} is independently selected from the group consisting of the ϵ-amino group of the adjacent lysine residue, [ϵ-γ]-Glu-Ac and [ϵ-γ]-Glu-[α-γ]-$(Glu)_{1-3}$-Ac (SEQ ID NO: 11), wherein [ϵ-γ] represents a peptide bond between the epsilon amino group of lysine and the gamma carboxyl group of the adjacent glutamate, [α-γ] represents a peptide bond between the alpha amino group of the first glutamate and the gamma carboxyl group of the second glutamate, and the subscript indicates that additional numbers of the designated amino acid can be linked to the first via conventional peptide bonds, and Ac represents an acetylated free amino group of the neighboring glutamate. As described above, modifications at each R position need not occur, but a modification at at least one R position must occur. With regard to the subscripted numbers, 1, 2, and 3 amino acids are contemplated, as well as large numbers of amino acids such as 4, 5, 6, etc.

The procytotoxic peptides of this invention may be chemically synthesized by standard solid phase procedures using the protection, deprotection and cleavage techniques and reagents appropriate to each specific amino acid or peptide. A combination of manual and automated (e.g., APPLIED BIOSYSTEM. 79 430A) solid phase techniques can be used to synthesize the novel peptides of this invention. For background on solid phase techniques, reference is made to Andreu et al., (1983) *Proc. Natl. Acad. Sci USA* 80: 6475-6479; Andreu et al., (1985) *Biochemistry* 24: 1683-1688; Fink et al. (June 1989) *Int. J. Peptide Protein Res.* 33: 412-421; Fink et al., (1989) *J. Biol. Chem.* 264: 6260-6267; each of which is incorporated herein by reference.

In one embodiment, the in vivo stability of the procytotoxin of the invention can be improved by adding an acetyl group to a modified cytotoxin. Indeed, the procytotoxins of the present invention that comprise a modified cytotoxin that is acetylated preferably have an increased half-life compared to procytotoxins that comprise a modified cytotoxin that is not acetylated. Enhanced stability is a feature that is particularly useful with products of the invention which are employed under conditions where they will be subject to hydrolysis by naturally occurring enzymes before they perform their desired physiological function. But, given that the instant medicaments are small peptides, which will generally have a comparatively short half-life, little, if any, destruction of non-target cells should occur if small amounts of activated cytolytic peptide escape the surface of the cancer cell.

Pharmaceutical Compositions

A further aspect of the present invention provides pharmaceutical compositions which comprise one or more procytotoxins of the invention and a pharmaceutically acceptable carrier or excipient.

While a procytotoxic peptide of the present invention can be administered, alone, to a patient, it is preferable to present the peptide as part of a pharmaceutical formulation. Pharmaceutically acceptable carriers typically include carriers known to those skilled in the art, including pharmaceutical adjuvants. Generally, these pharmaceutically acceptable carriers will include water, saline, buffers, and other compounds described, e.g., in the MERCK INDEX, Merck & Co., Rahway, N.J. See also BIOREVERSIBLE CARRIERS IN DRUG DESIGN, THEORY AND APPLICATION, Roche (ed.), Pergamon Press, (1987). These formulations typically comprise the pharmacological agent (i.e., the procytotoxin) in a therapeutically or pharmaceutically effective dose together with one or more pharmaceutically or therapeutically acceptable carriers and optionally other therapeutic ingredients. Various considerations are described, e.g., in Gilman et al. (eds) (1990) Goodman and Gilman's: THE PHARMACOLOGICAL BASES OF THERAPEUTICS, 8TH ED., Pergamon Press; NOVEL DRUG DELIVERY SYSTEMS, 2nd Ed., Norris (ed.) Marcel Dekker Inc. (1989), and Remington's Pharmaceutical Sciences, the full disclosures of which are incorporated herein by reference.

The compositions may be formulated in any pharmaceutical form appropriate for the desired route of administration. Examples of such compositions include preparations for parenteral administration such as sterile solutions, suspensions or emulsions. The compositions may also be manufactured in the form of sterile solid compositions which can be dissolved in sterile water, physiological saline or some other sterile injectable medium immediately before use. A preferred route of administration is via intraperitoneal, intravenous or subcutaneous injection.

Since the procytotoxins of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to one skilled in the art.

In all such compositions, the cytolytic peptides will normally be the principal physiologically active ingredient. The inventive peptides may be formulated, however, with additional pharmacological agents for combination therapies. When used in treating cancer, for example, they may be formulated with compatible conventional chemotherapeutic agents.

Methods for administration are also discussed in Gilman et al. (eds) (1990) and Norris (ed.), supra. In particular, the pharmaceutical composition of the invention may be administered parenterally, such as intravenously, subcutaneously, and intraperitoneally. See, for example, Wallace, B M, Lasker, J S, *Science,* 260:912-912 (1992). Liposomes may also be used to administer the procytotoxin of the invention (see Woodle, M C, Storm, G, Newman, M S, Jekot, J J, Collins, L R, Martin, F J, Szoka F C, *Pharmaceut. Res.* 9:260-265 (1992).

Methods of Treatment

The peptide protoxin of the present invention typically is converted, and thereby activated, into a cytotoxic peptide in a target cell-specific manner by an activity associated with the target cell. In other words, the target cell possesses a specific mechanism for converting the procytotoxin into a cytotoxin. The activated cytotoxic peptide acts on and destroys the target cell in a selective manner. Most conveniently, this cell-associated activity is a protease.

According to a preferred embodiment, a target cell contains a glutamate peptidase which cleaves gamma glutamate peptide bonds. When an acetylated γ-glutamate-masked cytolytic peptide is contacted with the target cell, the acetylated γ-glutamate residues are removed from the procytotoxin, and the resultant cytolytic peptide molecule causes lysis of the target cell. A non-target cell, which does not contain the glutamate peptidase, is unable to activate the procytotoxin and is thus unaffected by the procytotoxin.

A skilled person would readily recognize that if the glutamate residue is linked to the ε-amino group of a lysine, a peptidase, including the prostate specific membrane antigen discussed below, would be able to cleave the acetylated γ-linked glutamate residues regardless whether they are located at the C-terminus or the N-terminus of the cytotoxic peptide or somewhere in between.

In cases where the target cell has a protease activity that is the same or similar to conventional proteases, like chymotrypsin and trypsin, there should not be unwanted activation of the procytotoxin. That is, normally, chymotrypsin and trypsin are localized primarily in the intracellular environment, which is not accessible to the present procytotoxin medicaments. In the case of disorders where the target cells are associated with elevated levels of outer membrane-associated proteases, which are contacted with the procytotoxin due to their extracellular location, only the diseased cells will have the capability of activating the procytotoxin to its toxic form. Accordingly, the present procytotoxin are envisioned as having low levels of toxicity.

The present invention also comprehends a method for the treatment of cancers. According to one embodiment of the present invention, a pharmaceutical composition comprising the inventive procytotoxin is administered to a cancer patient, whose cancer cells are target cells possessing, for example, the requisite glutamate carboxypeptidase (or other enzyme for pro-drug conversion) for activating the procytotoxin.

Therapeutic treatment of cancer using the inventive cytolytic peptide-based procytotoxin is particularly advantageous because cytolytic peptides are known to be absorbed into the target cell membrane. Even after the target cell is lysed, therefore, the cytolytic peptides are prevented from acting on, and causing undesired destruction of, adjacent non-target cells.

The inventors recently have recognized that a range of cancer cells, beyond those of prostate specificity, apparently have the ability to cleave the subject acetylated γ-glutamate-masked cytolytic peptides. On the other hand, normal cells appear to lack this ability, rendering the inventive compounds highly effective in ablating cancer cells, yet leaving normal cells unaffected. Cancer cell types showing sensitivity to the inventive toxins include prostate, ovary, lung and melanoma. A search of public expressed sequence tag databases for PSMA-like molecules indicated that, whereas a number of cancers cells express proteins with significant degrees of homology to PSMA, normal cells do not. This observation likely explains the ability of the inventive molecules to act on a variety of tumor cells, while leaving normal cells unaffected.

Optimal delivery routes, dosages and regimens for a given mammalian host can be readily ascertained by one skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following non-limiting examples are given by way of illustration only and are not to be considered limitations of this invention, and there are many apparent variations within the scope of this invention. The examples illustrate activity of the compounds of this invention and are illustrative of the studies that the art has relied on for close to half a century as reasonably predictive of the efficacy of cancer chemotherapeutic compounds.

EXAMPLES

Example 1

Mouse Model for Human Prostate Cancer

LNCaP cells lot #3475262 (Catalog # CRL-1740) are received from ATCC, quickly thawed at 37° C. and placed in culture immediately. Cells are cultured in RPMI media (supplemented with 10% FBS, 50,000 units of Penicillin and 50,000 ug Streptomycin) and grown at 37° C. in the presence of 5% $CO_2$. Cells are passed when approximately 80% confluent until there are enough cells to do the in vivo studies.

Prior to tumor injection, in vitro studies are conducted to check the activity of the acetylated and non-acetylated procytotoxin, and to check the activity of the LNCaP cells for their ability to secrete PSA. Peptide activity is checked by a LDH Cytotoxicity Detection Kit (Roche).

20 nude mice are injected subcutaneously (right flank) with 0.5 ml of a 4 million cell/ml suspension (50% PBS 50% high concentration matrigel). Each mouse receives approximately 2 million cells. The mice are male, approximately 12 weeks of age and of the nude BalbC background.

Example 2

Preparation of an Acetylated γ-glutamate-Masked Amoebapore

The twenty-five amino acid, C-terminal amidated, amoebapore cytolytic peptide is synthesized by standard solid phase peptide synthesis, except that the ϵ amino group of the C-terminal lysine is blocked with a different blocking group from that used to block the ϵ-amino groups of the other two lysine residues in the peptide, so that the terminal ϵ block can be selectively removed. After selective removal of the blocking group from C-terminal lysine ϵ amino group, this amino group is linked to the γ carboxyl group of a first glutamate residue with blocked α amino and carboxyl groups by solution phase synthesis. This results in the addition of a γ glutamate linked side-chain glutamic acid residue.

The α amino group of this first glutamic acid residue is de-protected and a second glutamate residue is then linked to the de-protected α amino group via a γ glutamate linkage between the γ carboxyl group of the second glutamic acid residue and the α amino group of the first γ glutamate linked side-chain glutamic acid residue. The second γ-linked glutamate side-chain glutamic acid residue is also added by solution phase chemistry. The free amino group of the second glutamic acid residue is acetylated. If desired, further γ glutamate linked side-chain glutamic acid residues may be added in the same fashion.

Below is shown a diagram of the initial cytolytic peptide and the procytolytic peptide synthesized by the addition of the two γ glutamate linked side-chain glutamic acid residue to the ϵ amino group of the C-terminal lysine.

N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-$CONH_2$ (SEQ ID NO: 3).

Procytolytic Peptide:

N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp (SEQ ID NO:8)

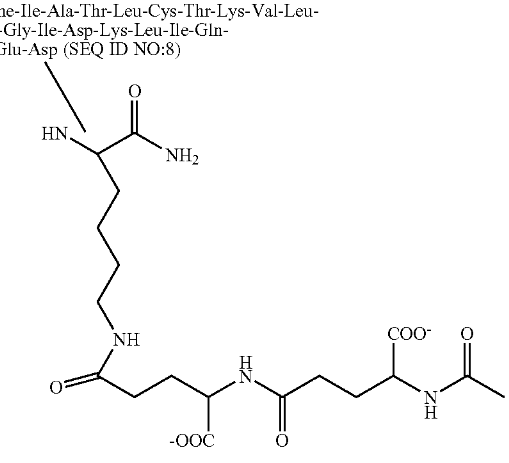

Example 3

In Vivo Treatment of a Prostate Tumor with a Procytotoxin 5 days following LNCaP tumor inoculation, mice are injected with an acetylated γ-glutamate-masked amoebapore, a non-acetylated γ-glutamate-masked amoebapore, and a control. Six control mice are injected with 200 μl of PBS and the remaining 14 mice are injected with 200 μl of a 1 mg/ml solution of either the acetylated or non-acetylated γ-glutamate-masked amoebapore peptide (i.e., 200 μg peptide per injection). Mice are injected intraperitoneally, twice per week. PSA levels are measured after three, five, and seven weeks of treatment. Lower PSA levels relative to control provide an objective indication that the procytotoxin is converted to its cytotoxic form and is able to lyse a target cell.

Results indicate that plasma PSA levels are lower following treatment with the non-acetylated and acetylated procytoxins when compared to control. However, intraperitoneal injection of the acetylated procytoxins lowered PSA levels to a greater extent than intraperitoneal injection of the non-acetylated procytotoxin.

Additionally, mice are weighed following 7 weeks of intraperitoneal injection of a non-acetylated procytotoxin or an acetylated procytoxin in a mouse model for prostate cancer. Results indicate that animals treated with either the acetylated or non-acetylated procytotoxin did not lose as much weight as the control animals. Additionally, animals treated with the acetylated procytotoxin experienced the least weight loss. Cachexia is a profound and marked state of constitutional disorder, representing general ill health. It is sometimes associated with an emaciated condition, such as cancerous cachexia seen in cases of a malignant tumor. Accordingly, weight loss may be an objective indicia of disease severity.

Example 4

Comparison of Acetylated vs. Non-Acetylated Procytotoxins in Lysing Human Prostate Cancer Cells in Vitro Non-acetylated γ-glutamate-masked amoebapore (a modified cytotoxin comprising one or more γ-linked glutamate residues linked via a peptide bond to the epsilon amino group of at least one lysine, preferably the C-terminal-most lysine), and acetylated γ-glutamate-masked amoebapore are compared in vitro for their ability to lyse LNCaP cells, as measured by percent lactic acid dehydrogenase (LDH) release. As indicated below, the non-acetylated procytotoxin can effectively lyse a greater percentage of LNCaP cells than the acetylated procytotoxin, thereby indicating that the non-acetylated procytotoxin may be more suited for treatment via other modes of administration, such as by direct application to a tumor site.

TABLE 2

| Procytotoxin | Concentration | % LDH Release |
|---|---|---|
| Acetylated procytotoxin | 160 μM | 29.94403 |
| Non-acetylated procytotoxin | 160 μM | 38.52612 |

What is claimed:

1. A procytotoxin comprising a peptide that comprises at least one lysine residue bound via a peptide bond to at least one acetylated amino acid via the ϵ-amino group of said lysine residue, wherein said peptide without said modification is a cytotoxic peptide, and wherein said at least one acetylated amino acid bound via the ϵ-amino group of said lysine residue acts to prevent the peptide from forming a lytically active conformation, wherein the cytotoxic peptide is a pore-forming cytolytic peptide.

2. The procytotoxin of claim 1, wherein the pore-forming cytolytic peptide is selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, E1Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perform, perfringolysin O of *Clostridium perfringens*, phallolysin, phallotoxin, and streptolysin.

3. The procytotoxin of claim 2, wherein the cytolytic peptide is an amoebapore.

4. The procytotoxin of claim 3, having the following structure: Gly-Phe-Ile-Ala-Thr-Leu-Cys-Thr-Lys{R}-Val-Leu-Asp-Phe-Gly-Ile-Asp-Lys{R}-Leu-Ile-Gln-Leu-Ile-Glu-Asp-Lys {R} (SEQ ID NO: 1), wherein at least one {R} is independently selected from the group consisting of [ϵ-γ]-Glu-Ac and [ϵ-γ]-Glu-[α-γ]-$(Glu)_{1-3}$-Ac (SEQ ID NO: 11), wherein: [ϵ-γ] represents a peptide bond between the epsilon amino group of lysine and the gamma carboxyl group of the adjacent glutamate and [α-γ] represents a peptide bond between the alpha amino group of the first glutamate and the gamma carboxyl group of the second glutamate, the subscript indicates that additional numbers of the designated amino acid can be linked to the first via conventional peptide bonds, and Ac represents an acetyl group bound to the free amino group of the last glutamate.

5. The procytotoxin of claim 2, wherein the cytolytic peptide is a melittin.

6. The procytotoxin of claim 5 consisting essentially of the following structure: Gly-Ile-Gly-Ala-Val-Leu-Lys{R}-Val-Leu-Thr-Thr-Gly-Leu-Pro-Ala-Leu-Ile-Ser-Trp-Ile-Lys {R}-Arg-Lys{R}-Arg-Gln-Gln (SEQ ID NO: 2), wherein at least one {R} is independently selected from the group consisting of [ϵ-γ]-Glu-Ac and [ϵ-γ]-Glu-[α-γ]-$(Glu)_{1-3}$-Ac (SEQ ID NO: 11), wherein: [ϵ-γ] represents a peptide bond between the epsilon amino group of lysine and the gamma carboxyl group of the adjacent glutamate, [α-γ] represents a peptide bond between the alpha amino group of the first glutamate and the gamma carboxyl group of the second glutamate, the subscript indicates that additional numbers of the designated amino acid can be linked to the first via conventional peptide bonds, and Ac represents an acetyl group bound to the free amino group of the last glutamate.

7. A procytotoxin comprising a peptide having at least one lysine residue bound via a peptide bond to at least one amino acid via the ϵ-amino group of said lysine residue, wherein said peptide without said modification is a cytotoxic peptide, and wherein said at least one amino acid bound via the ϵ-amino group of said lysine residue acts to prevent the peptide from forming a lytically active conformation, and wherein said procytotoxin has a structure selected from the group consisting of: N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-{[ϵ-γ]-Glu-[α-γ]-Glu-Ac}-$CONH_2$ (SEQ ID NO: 8) and $NH_2$-Gly-Ile-Gly-Ala-Val-Leu-Lys-Val-Leu-Thr-Thr-Gly-Leu-Pro-Ala-Leu-Ile-Ser-Trp-Ile-Lys{[ϵ-γ]-Glu-[α-γ]-Glu-Ac}-Arg-Lys-{[ϵ-γ]-Glu-[α-ϵ]-Glu-Ac}-Arg-Gln-Gln-COOH (SEQ ID NO: 10).

8. A pharmaceutical composition, comprising the procytotoxin of claim 1, and a pharmaceutically acceptable excipient.

9. A method for selectively destroying a target cell, comprising contacting the target cell with a procytotoxin, which comprises a cytotoxic peptide having at least one lysine residue bound via a peptide bond to at least one acetylated amino acid via the ϵ-amino group of said lysine residue, wherein the cell is a cancer cell and wherein the cytotoxic peptide is a pore-forming cytolytic peptide.

10. The method of claim 9, wherein said cancer cell is selected from the group consisting of prostate, ovarian, lung and skin cells.

11. The method of claim 9, wherein the pore-forming cytolytic peptide is selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perform, perfringolysin O, theta-toxin, of *Clostridium perfringens*, phallolysin, phallotoxin, and streptolysin.

12. he method of claim 11, wherein the cytolytic peptide is an amoebapore.

13. The method of claim , wherein the procytotoxin has the following structure: Gly-Phe-Ile-Ala-Thr-Leu-Cys-Thr-Lys {R}-Val-Leu-Asp-Phe-Gly-Ile-Asp-Lys {R}-Leu-Ile-Gln-Leu-Ile-Glu-Asp-Lys{R} (SEQ ID NO: 1), wherein at least one {R} is independently selected from the group consisting of [ϵ-γ]-Glu-Ac and [ϵ-γ]-Glu-[α-ϵ]-$(Glu)_{1-3}$-Ac (SEQ ID NO: 11), wherein: [ϵ-γ] represents a peptide bond between the epsilon amino group of lysine and the gamma carboxyl group of the adjacent glutamate, [α-ϵ] represents a peptide bond between the alpha amino group of the first glutamate and the gamma carboxyl group of the second glutamate, the subscript indicates that additional numbers of the designated amino acid can be linked to the first via conventional peptide bonds, and Ac represents an acetyl group bound to the free amino group of the last glutamate.

14. The method of claim 11, wherein the cytolytic peptide is a melittin.

15. The method of claim 14, wherein the procytotoxin consisting essentially of the following structure: Gly-Ile-Gly-Ala-Val-Leu-Lys{R}-Val-Leu-Thr- Thr-Gly-Leu-Pro-Ala-Leu-Ile-Ser-Trp-Ile-Lys{R}-Arg-Lys{R}-Arg-Gln-Gln (SEQ ID NO: 2), wherein at least one {R}is independently selected from the group consisting of-[ϵ-γ]-Glu-Ac and [ϵ-γ]-Glu-[α-γ]-$(Glu)_{1-3}$-Ac (SEQ ID NO: 11), wherein: [ϵ-γ] represents a peptide bond between the epsilon amino group of lysine and the gamma carboxyl group of the adjacent glutamate, [α-γ] represents a peptide bond between the alpha amino group of the first glutamate and the gamma carboxyl group of the second glutamate, the subscript indicates that additional numbers of the designated amino acid can be linked to the first via conventional peptide bonds and Ac represents an acetyl group bound to the free amino group of the last glutamate.

16. A method for selectively destroying a target cell, comprising contacting the target cell with a procytotoxin, which comprises a cytotoxic peptide having at least one lysine residue bound via a peptide bond to at least one amino acid via the ϵ-amino group of said lysine residue, wherein the cell is a cancer cell and the procytotoxin has the structure $NH_2$-Gly-Ile-Gly-Ala-Val-Leu-Lys-Val-Leu-Thr-Thr-Gly-Leu-Pro-Ala-Leu-Ile-Ser-Trp-Ile-Lys-{[ϵ-γ]-Glu-[α-γ]-Glu-Ac}-Arg-Lys-{[ϵ-γ]-Glu-[α-ϵ]-Glu-Ac}-Arg-Gln-Gln-COOH (SEQ ID NO: 10).

17. The procytotoxin of claim 1, wherein the pore-forming cytolytic peptide is selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perform, perfringolysin O of Clostridium perfringens, phallolysin, phallotoxin, and streptolysin.

18. The procytotoxin of claim 17, wherein the cytolytic peptide is an amoebapore.

19. The procytotoxin of claim 18, having the following structure: Gly-Phe-Ile-Ala-Thr-Leu-Cys-Thr-Lys{R}-Val-Leu-Asp-Phe-Gly-Ile-Asp-Lys{R}-Leu-Ile-Gln-Leu-Ile-Glu-Asp-Lys{R} (SEQ ID NO: 1), wherein at least one {R} is independently selected from the group consisting of [ϵ-γ]-Glu-Ac and [ϵ-γ]-Glu-[α-ϵ]-$(Glu)_{1-3}$-Ac (SEQ ID NO: 11), wherein [ϵ-γ] represents a peptide bond between the epsilon amino group of lysine and the gamma carboxyl group of the adjacent glutamate, [α-ϵ] represents a peptide bond between the alpha amino group of the first glutamate and the gamma carboxyl group of the second glutamate, the subscript indicates that additional numbers of the designated amino acid can be linked to the first via conventional peptide bonds, and Ac represents an acetyl group bound to the free amino group of the last glutamate.

20. A method for selectively destroying a target cell, comprising contacting the target cell with a procytotoxin, which comprises a cytotoxic peptide having at least one lysine residue bound via a peptide bond to at least one amino acid via the ϵ-amino group of said lysine residue, wherein the cell is a cancer cell and the procytotoxin has the structure N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-{[ϵ-γ]-Glu-[α-ϵ]-Glu-Ac}-$CONH_2$ (SEQ ID NO: 8).

21. A procytotoxin comprising a peptide having at least one lysine residue bound via a peptide bond to at least one- amino acid via the ϵ-amino group of said lysine residue, (i) wherein said peptide without the modification is a cytolytic peptide, (ii) wherein said at least one amino acid bound via the ϵ-amino group of said lysine residue acts to prevent the peptide from forming a lytically active conformation, and (iii) wherein said cytolytic peptide need not be internalized to cause target-specific cell death.

22. The procytotoxin of claim 21, wherein the cytolytic peptide is selected from the group consisting of amoebapore and melittin.

* * * * *